(12) United States Patent
Borgnine

(10) Patent No.: US 6,623,745 B2
(45) Date of Patent: Sep. 23, 2003

(54) EMOLLIENT

(75) Inventor: Tova Borgnine, Beverly Hills, CA (US)

(73) Assignee: TBH Marks, Inc., Wilmington, DE (US)

( * ) Notice: Subject to any disclaimer, the term of this patent is extended or adjusted under 35 U.S.C. 154(b) by 0 days.

(21) Appl. No.: 10/086,091

(22) Filed: Feb. 27, 2002

(65) Prior Publication Data

US 2002/0159959 A1 Oct. 31, 2002

Related U.S. Application Data

(60) Provisional application No. 60/272,164, filed on Feb. 27, 2001, provisional application No. 60/272,284, filed on Feb. 27, 2001, provisional application No. 60/272,172, filed on Feb. 27, 2001, and provisional application No. 60/272,285, filed on Feb. 27, 2001.

(51) Int. Cl.$^7$ ................................................ A61K 7/00
(52) U.S. Cl. ...................................... 424/401; 424/400
(58) Field of Search ................................ 424/400, 401

(56) References Cited

U.S. PATENT DOCUMENTS 5,053,222 A * 10/1991 Takasu et al. ............. 424/70.1
6,352,685 B2 * 3/2002 Hoshino et al. .............. 424/59

* cited by examiner

*Primary Examiner*—Shelley A. Dodson
(74) *Attorney, Agent, or Firm*—Caesar, Rivise, Bernstein, Cohen & Pokotilow, Ltd.

(57) ABSTRACT

The present invention is a compound containing a cactus extract, which moistens the skin when the skin is exposed to radiation, such as during radiation treatment, sunburn or other types of burns.

13 Claims, No Drawings

EMOLLIENT

This application claim benefit of Prov. No. 60/272,164 filed Feb. 27, 2001 and Prov. Nos. 60/272,284, 60/272,172, 60/272,285 all filed Feb. 27, 2001.

FIELD OF THE INVENTION

The present invention relates to a compound containing a cactus extract, which moistens the skin when the skin is exposed to radiation, such as during radiation treatment, sunburn or other types of burns.

BACKGROUND OF THE INVENTION

There is nothing presently available on the market to protect the skin after it has been exposed to radiation. There is a lack of moisture in the skin after it has been exposed to radiation.

Under normal conditions, the water content and vapor pressure of the epidermis are higher than the surrounding air and water evaporates from the surface of the skin. Skin becomes dry due to excessive loss of water from the stratum corneum when exposed to low relative humidities, insufficient hydration from the lower epidermal layers and/or air movement. Different journals have defined an emollient as a material which relieves dryness of skin or effects the softening of a dry corneum by inducing hydration. It is the decrease in the water content of the stratum corneum which is the main cause of the dry feeling in chapped skin.

SUMMARY OF THE INVENTION

The present invention relates to a Cactine emollient that keeps moisture in the skin when the skin is exposed to radiation. Cactine is derived from the roots of cacti plants. Cactine contains proteins, nutrients, and vitamins, especially vitamin E.

The present invention relates to an emollient, balm, or ointment. It is an object of the present invention to provide moisture to the skin while allowing the pores to breath. As an analogy, a pot of water on a stove will boil when heated. As long as the water is in the pot, the pot will not burn. The minute the water has evaporated from the pot, the pot will not only burn, but could conceivably get so hot that the bottom could fall out.

It is an object of the present invention to provide a compound that does not contain a sunscreen that treats radiation. It is an object of the present invention to provide a compound that does not create any soreness of the skin. It is an object of the present invention to provide a compound that does not peel the skin.

It is a further object of the invention to provide a compound that does not break down the skin. It is an object of the present invention to provide a compound at times when the skin feels dry.

It is an object of the present invention to improve the symptoms associated with cirrhosis, diaper rash, eczema and other related conditions.

DETAILED DESCRIPTION OF THE INVENTION

A patient was being treated for a lumpectomy in their breast by having six weeks of radiation therapy. The patient used the compound of the present invention on the area which was exposed to the radiation. The radiation caused the skin to dry. The compound provided moisture to the skin and abated the drying feeling. The skin exposed to the radiation did not breakdown in any way during this period. The compound of the present invention is not a sunscreen nor does it have a sunscreen added to it. The compound turned the skin coco brown. There was never any soreness of the skin, it never peeled and it never broke down.

In a preferred embodiment, the compound should be applied in the morning and during the radiation treatment, and applied after every treatment. The compound should also be applied in the evening before bed and can be used during the day whenever one feels the skin being dried.

In a preferred embodiment, the ingredients for the compound are:

Sweet Almond Oil (Prunus Amygdalus Dulcis)
Refined Safflower Oil (Carthamus Tinctorius)
Polydecene
Glyceryl Stearate
Refined Lanolin
Refined Beeswax
Glycerin
Petrolatum
Octyl Palmitate
Propylene Glycol
Deionized Water
Cactus Extract (Cereus Grandiflorus)
Orange Oil Natural (Citrus Aurantium Dulcis)
Vitamin E Tocopherol
Methyl Paraben
Sodium Hydroxide
Diazolidinyl Urea
Propyl Paraben In a preferred embodiment, to obtain the cactus extract, the cacti are cut into small pieces and the outer layer is trimmed. Cacti spines are removed. The outer skin of the cacti can be removed with a sharp instrument, such as a knife. The raw cacti are cut into small pieces. The cacti are placed in a blender. The blender is put on liquefy and the pieces are blended until liquefied.

To 275 grams of cacti is added approximately 775 grams of deionized water. The mixture is then blended on liquefy for approximately two minutes. If the mixture is not going to be used right away, it should be placed into a freezer until it is ready for use.

The following is an example of how the compound is made.

EXAMPLE 1

| | | |
|---|---|---|
| 1 | 8.6% | Cerasynt S.D. |
| 2 | 9.0% | Beeswax |
| 3 | 17.5% | Solid Petrolatum |
| 4 | 6.5% | Liquid Petrolatum |
| 5 | 13.0% | Lanolin |
| 6 | 6.5% | Glycerin |
| 7 | 25.3% | Almond Oil |
| 8 | 0.10% | Propyl Paraben |
| 9 | 0.20% | Methyl Paraben |
| 10 | 7.25% | Deionized water |
| 11 | 0.5% | Cactus Extract |
| 12 | 5.0% | Orange Extract |

The following is a preferred method for making the emollient of the present invention:

| | |
|---|---|
| 1 | Combine 1 to 8 and heat to 75 degrees Celsius |
| 2 | Combine 8, 9, 10 and heat to 75 degrees Celsius |
| 3 | Combine 2 into 7 and mix |
| 4 | Mix to temperature of 40 degrees Celsius and add 11 and 12 and mix. |

In a further embodiment the cactus extract is combined with beef bile and lanolin to treat the symptoms including alleviating the pain of cirrhosis, diaper rash, eczema and other related conditions.

In a preferred embodiment, the compound contains the following ingredients:

Sodium Tallowate
Sodium Cocoate
Water
Petrolatum
Glycerin
Lanolin
Sodium Chloride
Prickly Pear Extract (Opuntia Tuna)
Trisodium HEDTA
Titanium Dioxide
Iron Oxides

EXAMPLE 2

| Mixture B | |
|---|---|
| 1 | 70 kgs Rendered Fat |
| 2 | 50 kgs Coco Oil |
| 3 | 30 kgs NaOH |
| 4 | 10 kgs Sesame Seed Oil |
| 5 | 70 ltrs Water |

Heat 1, 2 and 4 to 60 degrees Celsius and agitate for 2 hours. Cool for one day until solid and then pulverize and dry. Add 3 and 5 and dissolve and add to heated 1, 2 and 4.

| Mixture A | |
|---|---|
| 1 | 20 gm Nopal (Cactus) |
| 2 | 1 kg Glycerin |
| 3 | 4 units Beef Bile |
| 4 | .5 kg Lanolin (Heated) |
| 5 | 100 ml Calomel Color |

Add 1, 2, 3 and 4 together and mix. Color can be added to the product by adding 5. Mixture A is poured into Mixture B and mixed thoroughly.

EXAMPLE 3

| | | |
|---|---|---|
| 1 | 94.245% | Deionized water |
| 2 | 2.0% | Cactus Extract |
| 3 | 1.0% | Germaben II |
| 4 | 0.25% | Yuccafoam |
| 5 | 1.0% | Aloe clear |
| 6 | 0.50% | Vitamin E |
| 7 | 0.005% | Polysorbate 20 |

Step 1

Place 1 into a Mixer. While mixing add item 2 and mix for approximately 2 minutes. Save some of the water for the pre-mix in Step 2. While mixing, add item 3 and mix for approximately three minutes. While mixing add item 4 and mix for approximately two minutes. While mixing add item 5 and mix for approximately two minutes.

Step 2

Premix item 6 and 7 and the reserved water from Step 1 into a separate container. Mix until uniform. Add the premix to the batch and mix for approximately five minutes.

The compound from example 3 can be used to keep moisture in the skin during radiation. It can further be used to increase circulation and provide an anti-inflammatory compound.

In a further embodiment, a compound containing the cactus extract of the present invention in combination with Agar and rice starch can be used as an anti-inflammatory compound.

The preferred ingredients for this compound are:

| | | |
|---|---|---|
| 1 | 3.0% | Agar/Agar (Karageenan) |
| 2 | 36.0% | Rice Starch |
| 3 | 0.3% | Dawicel 200 |
| 4 | 5.0% | Glycerin |
| 5 | 0.20% | Methyl Paraben |
| 6 | 0.10% | Propyl Paraben |
| 7 | | Deionized water |
| 8 | | Cactus Extract |
| 9 | | Color Fragrance |

Place Item 7 into a mixer. Add Item 3 and mix, and then add Item 6 and mix. Add Item 5 and Item 8 to mixture and mix well. Add Item 1 and mix. Add item 2 a little at a time and mix until smooth. Place batch in blender and blend until creamy.

What is claimed is:

1. A composition comprising a cactus meat homogenate, an emulsifying agent, a polar oil, a non-polar oil, a non-polar wax, a preservative, a humectant and water, wherein the composition is adapted to deter radiation from removing moisture from skin.

2. The composition of claim 1, further comprising proteins, nutrients and vitamins, including vitamin E.

3. The composition of claim 1, wherein the composition is an emollient, a balm or an ointment.

4. The composition of claim 1, wherein the composition does not contain a sunscreen.

5. The composition of claim 1, wherein the cactus meat homogenate is from a cactus root.

6. The composition of claim 5, wherein the cactus meat homogenate comprises cactine.

7. A composition comprising a cactus meat homogenate, beef bile, a polar oil, a non-polar oil, a preservative, a humectant, water and lanolin, wherein the composition is adapted to treat skin disorders including skin disorders caused by cirrhosis, diaper rash and eczema.

8. The composition of claim 7, further comprising rendered fat, coco oil, sodium hydroxide, sesame seed oil and glycerin.

9. A composition comprising sweet almond oil, refined safflower oil, polydecene, glyceryl stearate, refined lanolin, refined beeswax, glycerin, petrolatum, octyl palmitate, propylene glycol, deionized water, cactus meat homogenate, orange oil, vitamin E, methyl paraben, sodium hydroxide, diazolidnyl urea and propyl paraben, wherein the composition is adapted to deter radiation from removing moisture from skin.

10. A composition comprising glyceryl stearate, beeswax, solid petrolatum, liquid petrolatum, lanolin, glycerin, almond oil, propyl paraben, methyl paraben, deionized water, cactus meat homogenate and orange extract, wherein the composition is adapted to deter radiation from removing moisture from skin.

11. A composition comprising deionized water, cactus meat homogenate, Germaben II, Yuccafoam, Aloeclear, vitamin E and polysorbate 20, wherein the composition is an anti-inflammatory adapted to increase circulation in skin on which the composition is applied.

12. A composition comprising cactus meat homogenate, agar and rice starch, wherein the composition is a topical anti-inflammatory.

13. The composition of claim 12, further comprising Dawicel 200, glycerin, methyl paraben, propyl paraben and deionized water.

* * * * *